United States Patent [19]

Konrad et al.

[11] Patent Number: 4,828,568
[45] Date of Patent: May 9, 1989

[54] OXIDATION HAIR-DYEING PREPARATIONS

[75] Inventors: Guenther Konrad, Hilden; Hinrich Moeller, Monheim; Edgar Lieske, Duesseldorf, all of Fed. Rep. of Germany

[73] Assignee: Henkel Kommanditgesellschaft Auf Aktien, Duesseldorf, Fed. Rep. of Germany

[21] Appl. No.: 130,350

[22] Filed: Dec. 8, 1987

[30] Foreign Application Priority Data

Dec. 8, 1986 [DE] Fed. Rep. of Germany ....... 3641832

[51] Int. Cl.⁴ ........................ A61K 7/13; C07C 119/10
[52] U.S. Cl. ........................................... 8/408; 8/407; 8/424; 8/429; 564/274
[58] Field of Search .................. 8/407, 408, 424, 429; 564/274

[56] References Cited

U.S. PATENT DOCUMENTS 4,575,377  3/1986  Rose et al. ............................. 8/424

FOREIGN PATENT DOCUMENTS 2327987  1/1975  Fed. Rep. of Germany .......... 8/429
3545245  6/1987  Fed. Rep. of Germany .

*Primary Examiner*—Paul Lieberman
*Assistant Examiner*—Christine A. Skane
*Attorney, Agent, or Firm*—Ernest G. Szoke; Wayne C. Jaeschke; Norvell E. Wisdom, Jr.

[57] ABSTRACT

Oxidation hair-dyeing preparations which contain as couplers N-(2-4dihydroxbenzylidene)-amino compounds corresponding to the following formula

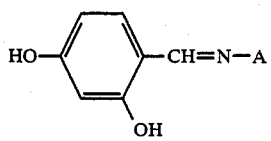

in which A is a group corresponding to one of the following formulae

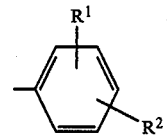

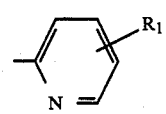

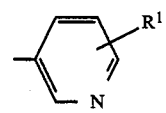

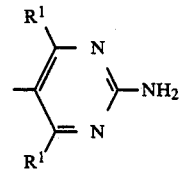

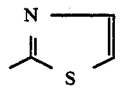

or salts thereof and the developers normally present in oxidation hair dyes. p-Phenylenediamine and derivatives thereof are particularly suitable as developers. Yellow to olive-brown colors of high fastness are obtained.

19 Claims, No Drawings

OXIDATION HAIR-DYEING PREPARATIONS

BACKGROUND OF THE INVENTION

1. Field of the Invention:

This invention relates to hair-dyeing preparations based on oxidation dyes. The hair-dyeing preparations in question contain oxidation dye precursors in a cosmetic carrier. The oxidation dye precursors used are developer substances and coupler substances which form dyes under the effect of oxidizing agents or atmospheric oxygen. Suitable cosmetic carriers for the oxidation dye precursors include creams, emulsions, gels, shampoos, foam aerosols or other preparations which are suitable for application to the hair.

2. Statement of Related Art:

By virtue of their bright colors and good fastness properties, oxidation dyes, which are formed by the oxidative coupling of one or more developer components with one another or with one or more coupler components, play a prominent part in the dyeing of hair. The developer substances normally used include primary, aromatic amines containing another free or substituted hydroxy or amino moiety in the para or ortho position, diaminopyridine derivatives, heterocyclic hydrazone derivatives, 3-aminopyrazolone derivatives and tetraaminopyrimidines. Useful couplers include m-phenylenediamine derivatives, napthols, resorcinol derivatives and pyrazolones.

Good oxidation dye precursors primarily have to satisfy the requirement of forming the desired shades of color with sufficient intensity during the oxidative coupling reaction. In addition, they must be readily taken up by human hair without excessive staining of the scalp. The hair colors produced must show high stability to heat and light and to the chemicals used in the permanent waving of hair. Finally, the oxidation hair dye precursors must be both toxicologically and dermatologically safe.

DESCRIPTION OF THE INVENTION

Other than in the operating examples, or where otherwise indicated, all numbers expressing quantities of ingredients or reaction conditions used herein are to be understood as modified in all instances by the term "about".

It has been found that hair-dyeing preparations based on oxidation dyes in a carrier which contains in addition to the developers normally present in oxidation hair-dyeing preparations, as oxidation dye couplers at least one N-(2,4-dihydroxybenzylidene)-amino compound corresponding to the formula

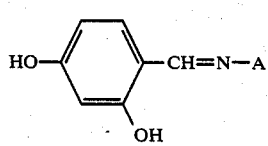

(I)

in which A is a moiety corredsponding to one of the following formulae

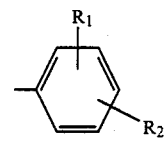

(II)

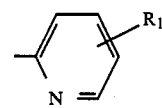

(III)

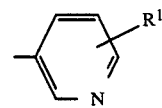

(IV)

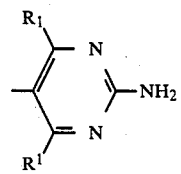

(V)

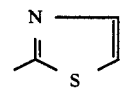

(VI)

wherein:

$R^1$ is hydrogen or a $C_{1-4}$ alkyl and $R^2$ is a $C_{1-4}$ alkyl, a $C_{1-4}$ alkoxy, —COOH, or —SO$_3$H, or salts thereof satisfy the above-mentioned requirements to a high degree.

$R^1$ and $R^2$ in formula II may be arranged in any position relative to one another and to the azomethine moiety; in formulae III and IV, $R^1$ may also be in any position on the pyridine nucleus. It is preferred to use compounds of formula I where A is formula II in which $R^1$ is hydrogen and $R^2$ is —OCH$_3$, —COOH or —SO$_3$H, or salts of these compounds.

Compounds corresponding to formula I are also suitable as substantive dyes. Hair-dyeing preparations containing substantive dyes corresponding to formula I, in which A is a group of formula II, are already the subject ot commonly assigned German patent application No. 35 45 245 published 25 June 1987. However, it unexpectedly has been found that the N-(2,4-dihydroxybenzylidene)-amino compounds corresponding to formula I also exhibit coupler properties, i.e. they form particularly intensive, natural oxidation hair colors having particularly good fastness properties by oxidative coupling with known developer components under the effect of oxidizing agents.

The N-(2,4-dihydroxybenzylidene)-amino compounds corresponding to formula I are preferably used in free form in the hair-dyeing preparations according to this invention, although the corresponding salts may also be used where acidic or basic groups are present. The compounds containing —COOH and —SO$_3$H substituents may be used in the form of the alkali or ammonium salts while the compounds where A is a group of formula V may also be used in the form of the hydrochlorides, sulfates, phosphates, acetates, propionates, lactates or citrates.

The developers present in the hair-dyeing preparations according to the invention may be aromatic amines containing one or more other NH$_2$ groups, NHR groups, $NR_2$ groups, where R is a $C_{1-4}$ alkyl group or a hydroxyalkyl group or a $C_{2-4}$ aminoalkyl group, aminophenols, aminophenol ethers, diaminopyridine derivatives or 2,4,5,6-tetraaminopyrimidine and derivatives thereof, such as 4,5-diamino-2,6-bismethylaminopyrimidine, 2,5-diamino-4-diethylamino-6-methylaminopyrimidine, 2,4,5-triamino-6-anilinopyrimidine, 2,4,5-triamino-6-morpholinopyrimidine, or 2,4,5-triamino-6-(2-hydroxyethyl)-aminopyrimidine.

Particularly valuable, natural yellow to olive-brown shades are obtained when the N-(2,4-dihydroxybenzylidene)-amino compounds of formula I are present in oxidation hair-dyeing preparations together with developers of the aromatic diamine type, more especially paraphenylenediamine and derivatives thereof.

Preferred developers of this type are, for example, p-phenylenediamine, p-tolylenediamine, N-methyl-p-phenylenediamine, N,N-dimethyl-p-phenylenediamine, N-hydroxyethyl-p-phenylenediamine, N,N-bis-(2-hydroxyethyl)-p-phenylenediamine, N-ethyl-N-(2-hydroxy-ethyl)-p-phenylenediamine, N,N-diethyl-2-methyl-p-phenylenediamine, 2-chloro-p-phenylenediamine, 2,6-dichloro-p-phenylenediamine, 2-chloro-6-methyl-p-phenylene-diamine, 2-methoxy-p-phenylenediamine, 2,5-diaminoanisole, 6-methoxy-3-methyl-p-phenylenediamine, N-(2-methoxyethyl)-p-phenylenediamine, N-(2-hydroxypropyl)-p-phenylenediamine, N-butyl-N-sulfobutyl-p-phenylenediamine, N-(p-aminophenyl)-N,N'-bis-($\beta$-hydroxyethyl)-1,3-diaminopropane or salts thereof with inorganic or organic acids.

In addition to the N-(2,4-dihydroxybenzylidene)-amino compounds corresponding to general formula I, the hair-dyeing preparations according to the invention may also contain other known (secondary) couplers which are necessary for modifying the colors and for producing natural tones. Standard coupler compounds of the type in question are, for example, other m-phenylenediamines, for example 2,4-diaminophenyl-2-hydroxyethylether, 2,4-diaminoanisole, or phenols, resorcinols, m-aminophenols, naphthols or pyrazolones.

If desired, substantive dyes may be additionally used for further modification of the colors. Suitable substantive dyes are, for example, nitrophenylenediamines, nitroaminophenols, anthraquinone dyes or indophenols.

In general, the N-(2,4-dihydroxybenzylidene)-amino compounds corresponding to formula I and the known couplers, if any, additionally present may be used in substantially molar quantities, based on the developers used. Although it has proven practical to use molar quantities, there is no disadvantage in using individual oxidation dye precursors in a slight excess, in which case the developers and couplers may be present in a molar ratio of 1:0.5-2. The N-(2,4-dihydroxybenzylidene)-amino compounds of formula I and the oxidation dye precursors or substantive dyes otherwise present in the hair-dyeing preparations do not have to be individual chemical compounds. Instead, mixtures of the couplers or developers may also be used in accordance with the invention.

In principle, the applied dye may be developed by oxidation with atmospheric oxygen. However, it is preferred to use at least one chemical oxidizing agent, particularly when, in addition to dyeing, it is desired to lighten the hair. Suitable oxidizing agents are, in particular, hydrogen peroxide or adducts thereof with urea, melamine or sodium borate as well as mixtures of these hydrogen peroxide adducts with potassium peroxydisulfate.

To produce the hair-dyeing preparations according to the invention, the oxidation dye precursors are incorporated in a suitable cosmetic carrier in the form of creams, emulsions, gels or even surfactant-containing, foaming solutions, such as shampoos, or other preparations which are suitable for application to the hair. Standard ingredients of cosmetic preparations such as these are, for example, wetting agents and emulsifiers, such as anionic, nonionic or ampholytic surfactants, for example fatty alcohol sulfates, alkane sulfonates, alpha-olefin sulfonates, fatty alcohol polyglycolether sulfates, ethylene oxide adducts with fatty alcohols, fatty acids and alkyl phenols, sorbitan fatty acid esters and fatty acid partial glycerides, fatty acid alkanolamides and also thickeners such as methyl or hydroxyethyl cellulose, starch, fatty alcohols, paraffin oils, fatty acids; perfume oils and hair care additives such as water soluble cationic polymers, protein derivatives, pantothenic acid and cholesterol.

The constituents of the cosmetic carriers are used in the usual quantities for producing the hair-dyeing preparations according to the invention. For example, emulsifiers are used in concentrations of from 0.5 to 30% by weight and thickeners in concentrations of from 0.1 to 25% by weight, based on the hair-dyeing preparation as a whole. The oxidation dye precursors are incorporated in the carrier in quantities of from 0.2 to 5% by weight and preferably in quantities of from 1 to 3% by weight, based on the hair-dyeing preparation as a whole. The N-(2,4-dihydroxybenzylidene)-amino compounds of formula I may be present in the hair-dyeing preparations according to the invention in quantities of from about 0.05 to 10 millimoles per 100 g of the hair-dyeing preparation.

Irrespective of the nature of the cosmetic composition, the hair-dyeing preparations according to the invention may be used in the form of creams, gels or shampoos in a mildly acidic, neutral or alkaline medium. The hair-dyeing preparations are preferably used at a pH in the range 8 to 10. They may be applied at temperatures in the range 15 to 40° C. After a contact time of about 30 minutes, the hair-dyeing preparation is removed by rinsing out from the hair to be dyed. The hair is then rewashed in a mild shampoo and dried. There is no need for rewashing with a shampoo in cases where a carrier of high surfactant content, for example a dye shampoo, has been used.

The following Examples are intended to illustrate the invention without limiting it in any way.

EXAMPLES

I. Preparation of N-(2,4-dihydroxybenzylidene)-amino compounds corresponding to formula I Products 1, 2 and 6 to 10 in Table I were prepared by combining ethanolic solutions of molar quantities of 2,4-dihydroxybenzaldehyde and
  (1) p-anisidine
  (2) m-anisidine
  (6) 2,6-dimethylanisidine
  (7) 2-aminothiazole
  (8) 2-aminopyridine
  (9) 3-aminopyridine
  (10) 2,5-diamino-4,6-dimethylpyrimidine.

The azomethines precipitated from the solution after a few hours at 20° C and were filtered off and washed with ethanol and dried.

Products 3, 4 and 5 of Table I were prepared by combining ethanolic solutions of molar quantities of 2,4-dihydroxy-benzaldehyde and
- (3) anthranilic acid
- (4) p-aminobenzoic acid and
- (5) sulfanilic acid.

After the reactants had been combined, the reaction mixture was heated for 5 hours. After cooling, the azomethines precipitated were filtered off, washed with ethanol and dried.

TABLE I

| Example | Azomethine Compound | Melting point | Appearance |
|---|---|---|---|
| 1. | N—(2,3-dihydroxybenzylidene-p-anisidine | beyond 90° C. | Yellow-brown crystals |
| 2. | N—(2,4-dihydroxybenzylidene)-m-anisidine | 151° C. | Grey-yellow crystals |
| 3. | N—(2,4-dihydroxybenzylidene)-anthranilic acid | above 250° C. | Yellow crystals |
| 4. | N—(2,4-dihydroxybenzylidene)-p-amino-benzoic acid | 218° C. | Yellow crystals |
| 5. | N—(2,4-dihydroxybenzylidene)-sulfanilic acid | above 250° C. | Yellow-orange crystals |
| 6. | N—(2,4-dihydroxybenzylidene)-2,6-dimethyl aniline | 145° C. | Light brown powder |
| 7. | 2,(2,4-dihydroxybenzylideneamino)-thiazole | beyond 80° C. | Yellow-brown crystals |
| 8. | 2-(2,4dihydroxybenzylideneamino)-pyridine | above 270° C. | Yellow crystals |
| 9. | 3-(2,4-dihydroxybenzylideneamino)-pyridine | beyond 180° C. | Yellow crystals |
| 10. | 2-amino-5-(2,4-dihydroxybenzylidene-amino)-4,6-dimethylpyrimidine | 205–206° C. with decomp. | Yellow crystals |

Performance tests

Hair-dyeing preparations according to the invention were prepared in the form of a hair dye cream emulsion having the following composition:

| | |
|---|---|
| $C_{12-14}$ Fatty alcohol | 10 g |
| $C_{12-14}$ Fatty alcohol + E.O. sulfate, Na salt, 28% | 25 g |
| Water | 60 g |
| Coupler (azomethine of Table 1) | 0.0075 mol |
| p-tolylenediamine (developer) | 0.0075 mol |
| $Na_2SO_3$ (inhibitor) | 1.0 g |
| Concentrated ammonia solution | to pH 9.5 |
| Water | q.s. ad 100 g |

The constituents were mixed together in the above order. After addition of the oxidation dye precursors and the inhibitor, the pH of the emulsion was first adjusted with concentrated ammonia solution, after which the emulsion was made up with water.

The oxidative development was carried out with 3% hydrogen peroxide solution as oxidizing agent. To effect this, 5 g of hydrogen peroxide solution (3%) were added to and mixed with 10 g of the emulsion.

The dye cream was applied to standardized, 90% gray, but not specially pretreated human hair and left thereon for 30 minutes at 27° C. After dyeing, the hair was rinsed, washed with a standard shampoo and then dried.

The results of the dyeing tests are shown in Table II.

TABLE II

| Example | Color of dyed strands |
|---|---|
| 1 | olive-brown |
| 2 | olive-brown |
| 3 | olive-brown |
| 4 | olive-yellow |
| 5 | olive-brown |
| 6 | olive-brown |
| 7 | olive-brown |
| 8 | yellow-brown |
| 9 | yellow-brown |
| 10 | olive-brown |

The colors of all strands dyed according to this invention desirably included olives and/or browns. Less desirable bright yellows were either absent or were muted. Although applied as a cream emulsion, there is no reason to believe that other compositions containing the invention hair dyes described above, would not be equally effective.

We claim:

1. In an oxidative hair dye composition comprising at least one coupler, at least one developer, and a liquid carrier, the improvement wherein
   said coupler is at least one N-(2,4-dihydroxybenzylidene)-amino compound of the formula, said at least one coupler and said at least one developer being present in a molar ratio of 1:0.5-2—.

in which A is a moiety corresponding to the following formula

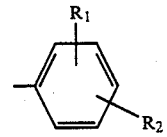

(II)

wherein:
   $R^1$ is hydrogen or a $C_{1-4}$ alkyl,
   $R^2$ is a $C_{1-4}$ alkyl, a $C_{1-4}$ alkoxy, —COOH, or —SO$_3$H; or a salt thereof, all ingredients being present in oxidative hair dye effective amounts, said at least one coupler and said at least one developer being present in a molar ratio of 1:0.5-2.

2. The composition of claim 1 wherein $R^1$ is hydrogen and $R^2$ is —COOH$_3$, —COOH, or —So$_3$H, or a salt thereof.

3. The composition of claim 2 wherein said couplers are in the form of their alkali or ammonium salts.

4. The composition of claim 1 wherein said coupler is at least one of:
   (1) N-(2,4-dihydroxybenzylidene)-p-anisidine;
   (2) N-(2,4-dihydroxybenzylidene)-m-anisidine;
   (3) N-(2,4-dihydroxybenzylidene)-anthranilic acid;

(4) N-(2,4-dihydroxybenzylidene)-p-amino-benzoic acid;

(5) N-(2,4-dihydroxybenzylidene)-sulfanilic acid; or (6) N-(2,4-dihydroxybenzylidene)2,6-dimethyl aniline.

5. The composition of claim 1 wherein said developer is at least one paraphenylenediamine or a derivative thereof.

6. The composition of claim 1 wherein said developer is at least one of:

p-phenylenediamine; p-tolylenediamine; N-methyl-p-phenylene-diamine; N,N-dimethyl-p-phenylenediamine; N-hydroxyethyl-p-phenylenediamine; N,N-bis-(2-hydroxyethyl)-p-phenylenediamine; N-ethyl-N-(2-hydroxyethyl)-p-phenylenediamine; N,N-diethyl-2-methyl-p-phenylenediamine; 2-chloro-p-phenylenediamine; 2,6-dichloro-p-phenylenediamine; 2-chloro-6-methyl-p-phenylene-diamine; 2-methoxy-p-phenylenediamine; 2,5-diaminoanisole; 6-methoxy-3-methyl-p-phenylenediamine; N-(2-methoxyethyl)-p-phenylenediamine; N-(2-hydroxypropyl)-p-phenylenediamine; N-butyl-N-sulfobutyl-p-phenylenediamine; N-(p-aminophenyl)-N,N'-bis-($\beta$-hydroxyethyl)-1,3-diaminopropane; or salts thereof with inorganic or organic acids.

7. The composition of claim 4 wherein said developer is at least one of:

p-phenylenediamine; p-tolylenediamine; N-methyl-p-phenylene-diamine; N,N-dimethyl-p-phenylenediamine; N-hydroxyethyl-p-phenylenediamine; N,N-bis-(2-hydroxyethyl)-p-phenylenediamine; N-ethyl-N-(2-hydroxyethyl)-p-phenylenediamine; N,N-diethyl-2-methyl-p-phenylenediamine; 2-chloro-p-phenylenediamine; 2,6-dichloro-p-phenylenediamine; 2-chloro-6-methyl-p-phenylene-diamine; 2-methoxy-p-phenylenediamine; 2,5-diaminoanisole; 6-methoxy-3-methyl-p-phenylenediamine; N-(2-methoxyethyl)-p-phenylenediamine; N-(2-hydroxypropyl)-p-phenylenediamine; N-butyl-N-sulfobutyl-p-phenylenediamine; N-(p-aminophenyl)-N,N'-bis-($\beta$-hydroxyethyl)-1,3-diaminopropane; or salts thereof with inorganic or organic acids.

8. The composition of claim 1 wherein at least one secondary coupler is present in a color-modifying effective amount, which coupler is a metaphenylenediamine, 2,4-diaminoanisole, phenol, resorcinol, meta-aminophenol, napthol, or pyrazolone.

9. The composition of claim 7 wherein at least one secondary coupler is present in a color-modifying effective amount, which coupler is a metaphenylenediamine, 2,4-diaminoanisole, phenol, resorcinol, meta-aminophenol, napthol, or pyrazolone.

10. The composition of claim 1 wherein at least one substantive dye is also present in a color-modifying effective amount, which dye is a nitrophenylenediamine, nitroaminophenol, anthraquimone, or indophenol.

11. The composition of claim 7 wherein at least one substantive dye is also present in a color-modifying effective amount, which dye is a nitrophenylenediamine, nitroaminophenol, anthraquimone, or indophenol.

12. The composition of claim 9 wherein at least one substantive dye is also present in a color-modifying effective amount, which dye is a nitrophenylenediamine, nitroaminophenol, anthraquimone, or indophenol.

13. The composition of claim 1 wherein the oxidative effect is achieved by including therein an oxidative-effective amount of a chemical oxidizing agent.

14. The composition of claim 13 wherein the chemical oxidizing agent is at least one of: hydrogen peroxide or adducts thereof with urea, melamine, or sodium peroxide, as well as mixtures thereof with potassium peroxydisulfate.

15. The composition of claim 1 wherein the total content of oxidation dye precursors is 0.2 to 5.0% by weight, based on the total hair dyeing composition.

16. The composition of claim 15 wherein the total content of oxidation dye precursors is 0.2 to 5.0% by weight, based on the total hair dyeing composition.

17. The composition of claim 1 wherein said coupler is present in about 0.05 to 10.0 millimoles per 100 g of the composition.

18. The composition of claim 16 wherein said coupler is present in about 0.05 to 10.0 millimoles per 100 g of the composition.

19. A method for dyeing hair comprising applying thereto a hair-dyeing effective amount of the composition of claim 1, permitting said composition to remain on said hair for a hair-dyeing effective amount, and removing said composition from said hair.

* * * * *

UNITED STATES PATENT AND TRADEMARK OFFICE
CERTIFICATE OF CORRECTION

PATENT NO. : 4,828,568

DATED : May 9, 1989

INVENTOR(S) : Guenther Konrad, Hinrich Moeller, Edgar Lieske

It is certified that error appears in the above-identified patent and that said Letters Patent is hereby corrected as shown below:

In Claim 2, at Col. 6, line 60, "COOH$_3$" should read --OCH$_3$--.

Signed and Sealed this

Thirteenth Day of March, 1990

Attest:

JEFFREY M. SAMUELS

*Attesting Officer*      *Acting Commissioner of Patents and Trademarks*